United States Patent [19]

Stim

[11] 4,187,849
[45] Feb. 12, 1980

[54] SUCTION CURETTAGE DEVICE WITH VALVE CONTROL AND SUPPORT MEANS FOR DIFFERING DIAMETER TUBES

[76] Inventor: Edward M. Stim, 1120 Lexington Ave., New York, N.Y. 10021

[21] Appl. No.: 928,806
[22] Filed: Jul. 28, 1978
[51] Int. Cl.[2] .............................................. A61M 1/00
[52] U.S. Cl. .................... 128/278; 128/234
[58] Field of Search .............. 128/2 F, 276, 277, 278, 128/304, 234, DIG. 5; 222/506, 545; 285/12, 177; 251/148

[56] References Cited

U.S. PATENT DOCUMENTS

| | | | |
|---|---|---|---|
| 3,747,812 | 7/1973 | Kauman et al. | 128/218 NV |
| 3,834,372 | 9/1974 | Turney | 128/274 |
| 3,957,082 | 5/1976 | Fuson et al. | 128/274 |
| 4,082,095 | 4/1978 | Mandelson | 128/274 |

Primary Examiner—Robert W. Michell
Assistant Examiner—J. L. Kruter
Attorney, Agent, or Firm—Barry Evans

[57] ABSTRACT

A device for performing suction curettage procedures includes a housing having at least one port formed therein through which the interior of the housing communicates with a source of suction. A selectively positionable suction tube support member is mounted in the housing and has a plurality of tube support bores of different diameters formed therein adapted to be selectively aligned between the port and a diametrically opposed opening in the housing. Each of the bores is adapted to receive at least one differently sized suction tube therein through the housing opening so that different tubes may be selectively connected to the housing and the source of suction. In the preferred embodiment of the invention at least a portion of each of the housing bores are tapered so that at least two differently sized suction tubes can be mounted in each bore.

22 Claims, 12 Drawing Figures

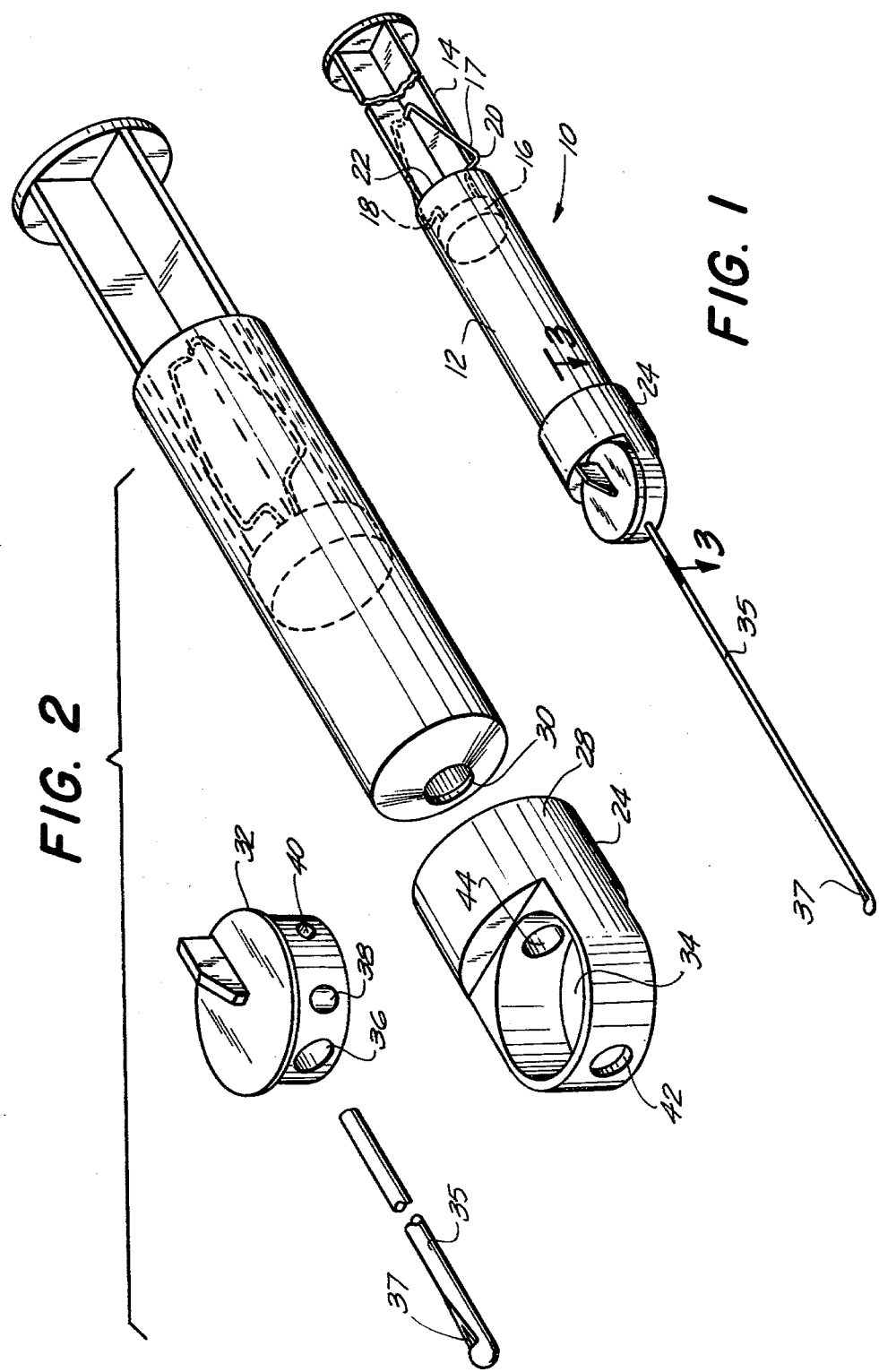

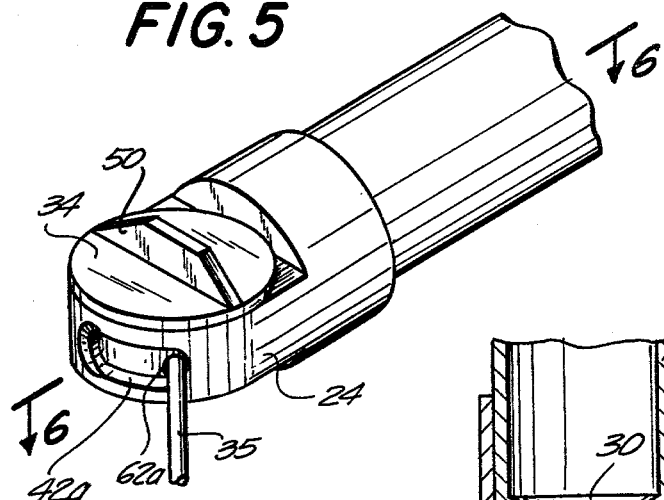
FIG. 5
FIG. 6
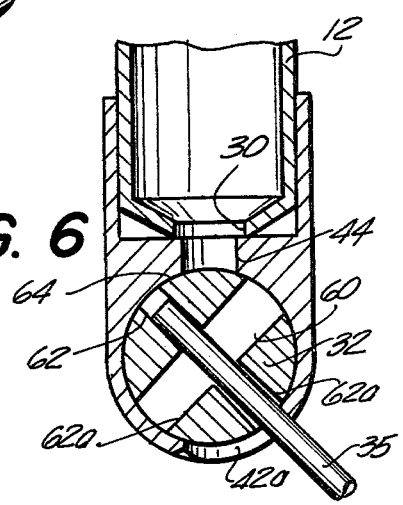
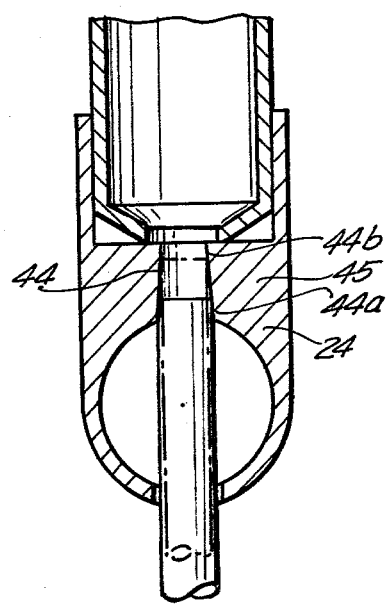
FIG. 7
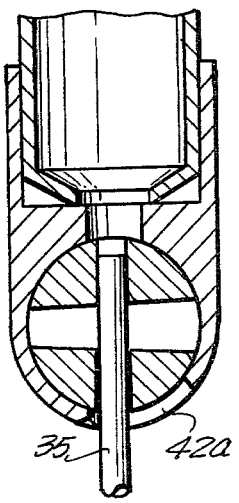
FIG. 8

SUCTION CURETTAGE DEVICE WITH VALVE CONTROL AND SUPPORT MEANS FOR DIFFERING DIAMETER TUBES

The present invention relates to a device for use in performing uterine curettage procedures, and in particular to a device, for use with hand aspirators, which enables a variety of different sized curettes or cannulas to be used with a single instrument.

Present day techniques for performing uterine curettage procedures typically utilize an electric vacuum pump as a suction aspirator to apply suction through a relatively rigid curette or cannula to the uterine cavity. Recently however hand syringes, originally developed for use in blood removal and injections, have been modified for use as suction aspirators to provide a small simple inexpensive and portable vacuum source. One such apparatus is disclosed for example in U.S. Pat. No. 3,747,812 to Karman et al.

Typically a flexible intra-uterine curette or cannula having a non-perforating tip is used with such syringes to eliminate uterine perforation. It has been found that the use of this type of soft suction curette design eliminates excessive endometrial removal and myometrial damage. Also, the soft cervical dilation eliminates cervical muscle damage and later cervical incompetence. And, the hand aspirator arrangement eliminates potentially fatal air embolisms that have become associated with the use of electrical vacuum pumps.

Even with the numerous advantages of the use of hand syringes for uterine curettage procedures, their use has been somewhat limited because of the absence of an instrument that can conveniently adapt the inlet of the syringe to the outlet of suction curettes and cannulas of a sufficiently large size required for a number of different medical procedures without creating a bottleneck to tissue flow through the system into the syringe.

Accordingly it is an object of the present invention to adapt conventional syringes for use as suction aspirators in suction curettage operations which use a variety of different sized curettes or cannulas.

A further object of the present invention is to provide a single instrument that will accept a series of suction curettes or cannulas of a full range of sizes.

Another object of the present invention is to provide a connection arrangement between a suction aspirator and a curette or curettes of different sizes, without any bottleneck to flow of tissue therebetween.

Another object of the present invention is to provide a suction curettage apparatus operable by hand and including control means for allowing the vacuum to be preset and held before insertion of the curette into the uterine cavity.

Another object of the present invention is to provide a hand operated suction curettage device which is adapted to use a plurality of different sized curettes.

Another object of the present invention is to provide a device of the character described which is relatively inexpensive to manufacture and is reliable in use.

A still further object of the present invention is to provide a device for forming a connection between a series of suction curettes or cannulas and an aspirator such as a syringe.

In accordance with an aspect of the present invention a device for use in performing suction curettage procedures is provided which includes a housing having at least one port formed therein through which the interior of the housing may communicate with a source of suction such as, for example, a hand operated syringe or aspirator. The housing includes an opening formed therein diametrically opposed to the suction port that permits a variety of different sized curettes or cannulas to be inserted into the housing. A suction tube or cannula support member is rotatably mounted in the housing and has a plurality of intersecting and generally radially extending tube support bores of different diameters formed therein. Each of these bores is adapted to be aligned between the housing and the port opening to receive a cannula or tube and frictionally retain it within the support member in communication with the housing bore and the source of suction. Each of the bores is adapted to receive at least one differently sized suction tube therein so that a variety of tubes may be selectively connected to the housing and the source of suction. In one embodiment of the invention the bores of the support member are tapered so that each bore may frictionally receive at least two differently sized cannulas. And, in another embodiment of the invention a valve arrangement is provided to enable the physician to selectively shut off the suction from the aspirator to the cannula through a valve arrangement closing the port of the housing.

The above, and other objects, features and advantages of this invention will be apparent in the following description of an illustrative embodiment thereof, which is to be read in connection with the accompanying drawings, wherein:

FIG. 1 is a perspective view of a suction curettage device constructed in accordance with the present invention;

FIG. 2 is an enlarged exploded perspective view of the device shown in FIG. 1;

FIG. 5 is a partial perspective view of a connection housing constructed in accordance with another embodiment of the present invention;

FIG. 6 is a sectional view taken along line 6—6 of FIG. 5 showing the manner in which the vacuum port of the housing is selectively closed;

FIG. 7 is a sectional view similar to FIG. 6 showing the housing port open;

FIG. 8 is a sectional view similar to FIG. 7 of another embodiment of the invention with the tube support member removed;

Figure 3:
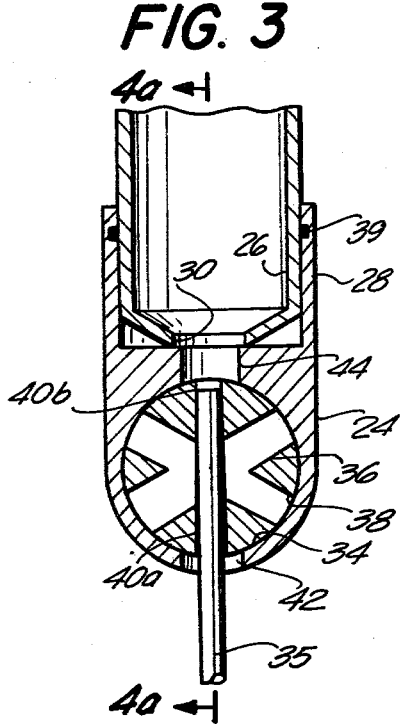
FIG. 3 is a partial sectional view of the housing which connects a cannula to the syringe taken along line 3—3 of FIG. 1.

Referring now to the drawings in detail, and initially to FIG. 1 thereof, a suction curettage apparatus 10 constructed in accordance with the present invention includes a syringe body 12, of generally conventional construction, formed of a plastic material and slidably receiving a piston rod 14 therein. The inner end of the piston rod includes a piston 16 which forms a substantially air tight seal with the interior of the syringe body. By withdrawing the piston from the syringe body, with the forward end of the syringe closed as described hereinafter, a vacuum is produced within the syringe. The vacuum is maintained and the piston is held against inadvertent depression into the syringe body by a pair of spring arms 18 which spring out when the piston is fully withdrawn into the position shown in FIG. 1, so that the arm sections 20 thereof engage the upper edge 22 of the syringe and prevent depression of the piston. This avoids inadvertent discharge of tissue drawn into the syringe during the curettage procedure. As seen in FIG. 2, the spring arms 18 are compressed within the syringe body 12 when the piston rod 14 is in its inner position.

The curettage device of the present invention also includes an adaptor and connection housing 24 removably mounted on the forward end 26 of the syringe body. This adaptor housing is constructed to enable the physician to connect a variety of different sized suction tubes to the syringe and to conveniently change the tube size during the curettage procedure without the creation of bottlenecks to tissue flow through the suction tube into the syringe body.

Housing 24 includes a generally cylindrical sleeve section 28 which fits over the forward end 26 of the syringe body with an air tight seal. In this regard, the foward end 26 of the syringe is preferably formed with an enlarged opening 30 therein that has a diameter which is larger than the internal diameter of any of the suction tubes adapted to be connected to housing 24. A rotary tube support member 32 is rotatably and removably received within a generally cylindrical well 34 in the forward end of housing 24. This support member has a plurality of bores 36, 38, 40 formed therein which extend along diameters of the support member in order to provide communication between a forward opening 42 in the housing and a through port 44 in the rear of the housing which communicates through the opening 30 with syringe body 12. The bores 36–40 have differing diameters in order to receive and support different diameter suction curettage tubes as described hereinafter. The openings 42 and the bore 44 each have a diameter which is greater than the outer diameter of the largest curettage tube to be mounted in support member 32, again to avoid bottlenecks to tissue flow passing through a suction curettage tube 35 to the syringe 12.

The hollow tubes 35 used with the apparatus of the present invention are preferably flexible tubes that have sufficient flexibility to bend against the resistance of the uterine wall, but not so flexible that they cannot hold their straightness against gravity. It has been found that polyethylene tubes provide the desired characteristics for curettage suction tubes. The tubes are provided in a variety of different external diameters, with their internal diameters varying in accordance with their outside diameter. The different sizes are provided with size numbers corresponding generally to their outside diameter dimension in millimeters. A typical size range used in suction curettage procedures is set forth in the following table:

TABLE I

| Size # | Outside Diameter | Inside Diameter | Wall Thickness |
| --- | --- | --- | --- |
| 3 | 3.00 mm | 2.00 mm | 0.50 mm |

TABLE I-continued

| Size # | Outside Diameter | Inside Diameter | Wall Thickness |
| --- | --- | --- | --- |
| 4 | 4.00 | 3.00 | 0.50 |
| 5 | 5.00 | 3.80 | 0.60 |
| 6 | 6.00 | 4.80 | 0.60 |
| 7 | 7.00 | 5.60 | 0.70 |
| 8 | 8.00 | 6.40 | 0.80 |
| 9 | 9.00 | 7.20 | 0.90 |
| 10 | 10.00 | 8.20 | 0.90 |
| 11 | 11.00 | 9.20 | 0.90 |
| 12 | 12.00 | 10.20 | 0.90 |

These tubes are generally straight and have one or more suction openings 37 formed therein near their forward ends in a conventional manner.

In accordance with a feature of the present invention the tube support housing 24 is adapted to conveniently receive and support different sized tubes, without bottleneck to tissue flow. In the illustrative embodiment of the invention the support member is adapted to support at least six different diameter tubes.

As illustrated in FIG. 3, housing 24 receives in its rear sleeve portion 28 the forward end 26 of the syringe 12. Preferably the sleeve 28 includes an inner O-ring 39 which forms a substantially air tight seal about the outside of the syringe body. Housing port 44 provides communication between syringe 26 through opening 30 to the well 34 of the housing. When one of the bores 36, 38 or 40 of the tube support member 32 is aligned with port 44 and forward opening 42 of housing 24 direct access is provided to the interior of syringe body 12. By inserting a suction tube 35 in the bore aligned with opening 42 in port 44 the suction curettage procedure can be performed.

Figure 4A:
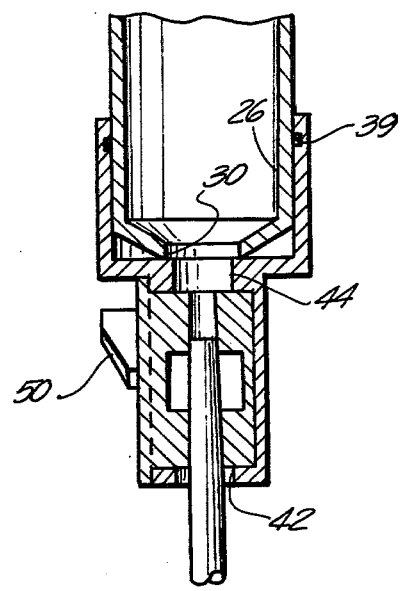
FIG. 4A is a sectional view taken along line 4A—4A of FIG. 3 showing a different sized cannula mounted in the same bore as the cannula shown in FIG. 3.

In accordance with an aspect of the present invention each of the bores 36–40 is dimensioned to receive therein at least two differently sized suction tubes, with each bore being adapted to receive different pairs of tubes of adjacent sizes. That is, for example as seen in FIG. 3, bore 40, the smallest of the three bores shown, has a forward end 40a whose diameter is relatively constant and is greater than the diameter of the largest suction tube to be supported therein (for example a No. 4 size tube). The rearward end of the bore 40b is tapered from its forward end at a diameter which is the same as that of the forward end 40a of the bore, to a rear end adjacent port 44 which is slightly smaller than the outside diameter of the next smaller sized tube (a No. 3 tube) but larger than the inside diameter of that smaller tube. In this manner, when a No. 3 tube is inserted through opening 42 into bore 40 it will seat in frictional engagement within the rear end 40b of the bore and be held there in a fixed position with a frictional and relatively air tight seal. The tube will penetrate almost to the end of bore section 40b, because it is the smaller of the tubes, yet no bottleneck will be provided to tissue flow since the remaining diameter of the bore is larger than the inner diameter of the tube. Of course when a larger size, No. 4 tube, is inserted in the bore 40 (see FIG. 4A) it will not penetrate as deeply into the section 40b of the bore.

Figure 4C:
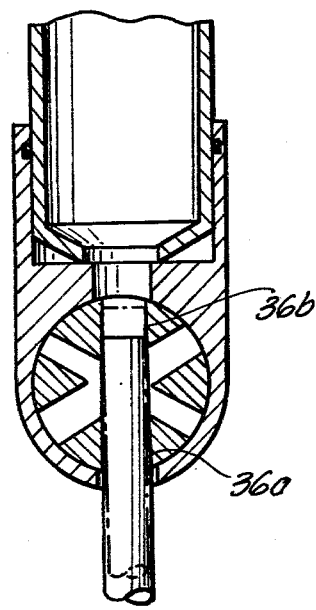
FIG. 4C is a sectional view similar to FIG. 4B showing the support of the next two larger sized cannulas in the third bore of the suction tube support member.
Figure 4B:
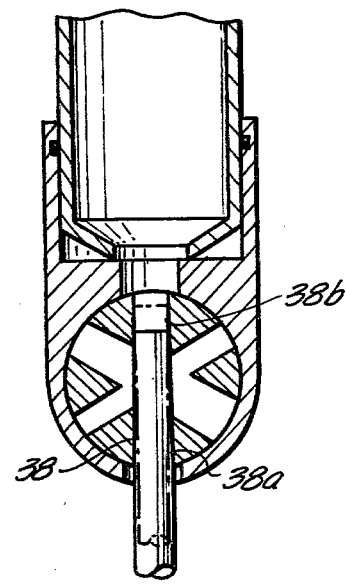
FIG. 4B is a view similar to FIG. 3 showing, in solid and phantom lines, two larger cannulas mounted in the next largest bore of the suction tube support member of the housing.

The other bores 36 and 38 intersect bore 40, as seen in FIGS. 3, 4b and 4c. Bore 38 has a forward end 38a whose diameter is slightly larger than the outside diameter of the largest suction tube to be received therein (a No. 6 tube in this embodiment). While its rear end 38b has a forward portion whose diameter is the same as that of the bore section 38a, but which tapers to a diameter that is smaller than the outside diameter of the smallest tube to be inserted therein (a No. 5 tube) but slightly larger than the inside diameter of that smaller tube. Thus, as illustrated in FIG. 4B, the No. 5 (shown in phantom lines) and No. 6 (shown in solid lines) tubes can be inserted in bore 38 in frictional engagement therein, without a bottleneck. Finally, bore 36, the largest of the three bores, has a forward end 36a (FIG. 4C) whose outer diameter is slightly larger than the largest diameter tube to be inserted therein (in this embodiment a No. 8 tube) while the diameter of its rear end 36b has a forward end whose diameter is the same as that of the forward section 36a but which tapers rearwardly to a diameter which is smaller than the outside diameter of the smallest tube to be inserted therein (a No. 7 tube in this embodiment) but larger than the needle diameter of that tube. Thus, as seen in FIG. 4B these two tubes may also be inserted in a friction tight seal within the tube support member.

In use, the physician places housing 24 on the forward end of syringe body 12 and rotates the tube support member in the recess 34 by using the conveniently located handle 50 thereon to align the bore which will support the suction tube he intends to use with opening 42 and port 44. He then places the inner end of the suction tube through opening 42 into the selected bore, until a good frictional engagement is achieved between the inner end of the tube and the rear section of the selected bore. The physician then inserts the suction tube, using customary procedures, through the cervix into the uterus of the patient. With the opened end of the suction tube within the uterus, the physician can now produce a suction within the syringe body by retracting the piston until springs 18 pop out of syringe body 12. This produces an adequate suction to perform the suction curettage procedure, which then proceeds in a conventional manner.

Should the physician find it necessary to use a suction tube of a different size, the suction tube is withdrawn and removed from the housing 24. The next larger tube size is then placed in the same bore, if appropriate, or the rotary support member is turned to align the next appropriate sized bore with opening 42 and port 44. The selected larger (or smaller) suction tube is then mounted in the housing. If necessary the housing can be removed from the syringe in order to permit the syringe to be emptied, by depression of the piston rod into the syringe body (This depression also enables the physician to reestablish the vacuum in the syringe after the new suction tube is inserted int the uterus). Thereafter the housing is remounted on the syringe and the suction tube inserted in the uterus and the vacuum produced again by retraction of the piston.

Another embodiment of the present invention is illustrated in FIGS. 5-7 of the drawings, which shows an arrangement that permits the physician to change suction tubes without breaking the suction in the syringe body and to produce suction within the syringe body before insertion of the suction tube into the uterus.

In this embodiment of the invention the housing 24 includes an elongated, generally oval shaped opening 42a at its forward end while the tube support member 34 has only a pair of bores 60, 62 formed therein to provide relatively wide arcuate surfaces 64 between the bores. As in the prior embodiment, each of the bores is provided with a forward section 60a, 62a, and a rearward section which tapers. The forward section has an outside diameter which is slightly larger than the diameter of the largest tube to be inserted therein, while the rear section of the bore has a forward portion which has the same diameter as the forward section of the bore, and a rear portion which has a diameter that is smaller than the outside diameter of the smallest suction tube to be inserted therein but larger than the inside diameter of that tube. With this arrangement, the physician can turn support member 34, using handle 50, to a position wherein the port 44 of the housing 24 is closed off, as seen in FIG. 6. In this position the piston rod can be retracted to produce a suction within syringe 12. Either before or after the vacuum in the syringe is produced, the selected suction tube 35 is inserted in the port 62. In this position the suction tube can then be inserted through the cervix into the uterus. Once the inner end of the suction tube is properly inserted, the physician will hold the handle 50 of support member 34 and rotate the syringe to align bore 62 with port 44. In the position shown in FIG. 5 and 6 the syringe would be rotated in a counterclockwise direction until bore 62 is aligned with port 44, as shown in FIG. 7. Then, if during the procedure the physician determines that the next larger sized suction tube is required, he reverses the procedure by holding the tube support member at handle 50 and rotating the syringe in a clockwise direction, to close off port 44. He can then withdraw the instrument from the patient, without breaking the suction within syringe 12, remove tube 35 and replace it with a larger sized tube, reinsert it in the patient and continue the procedure.

In another embodiment of the invention illustrated in FIG. 8, the port 44 may itself be formed with a tapered diameter, to permit the physician to connect even larger sized tubes to the syringe. In this embodiment of the invention the base wall 45 of the housing is made somewhat thicker than the base wall of the embodiment shown in FIGS. 1-7, and port 44 is provided with an interior diameter at its forward end 44a which is slightly larger than the largest sized tube (a No. 12 tube) to be used with the housing. The inner end 44b of the bore has a diameter which is smaller than the outside diameter of the smallest tube to be supported therein (for example a No. 10 tube) but larger than the inner diameter of that tube.

With this arrangement, if the physician finds it is necessary to use a suction tube larger than any of the tubes that will fit in the rotary support member 32, he can simply remove the rotary support member by lifting it out of recess 34 and then insert the selected suction tube through opening 42 directly into bore 44. In this regard it should be noted that the rotary tube support member 32 is carefully machined (of metal or plastic) to fit tightly within recess 34 in order to form an air tight seal therewith; but there is no fixed connection between the rotor and the housing, in order to permit the rotary support member to be removed axially therefrom.

It is also to be understood that while the description herein has been discussed the dimensioning of the various tube support bores in the rotary member and in the base 45 of the support housing as being adapted to receive and support two differently sized support tubes, it is contemplated that these bores may be tapered in varying dimensions to selectively support more than two differently sized support suction tubes.

Figure 9:
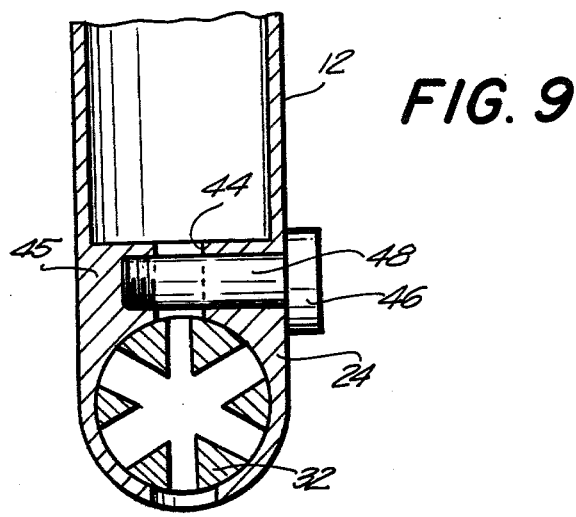
FIG. 9 is a sectional view similar to FIG. 8 of another embodiment of the present invention using a different valve means.

In another embodiment of the invention illustrated in FIG. 9, a somewhat different type of valve arrangement is provided to permit the physician to create a vacuum within syringe 12 prior to insertion of the suction tube into the uterus. In addition, in this embodiment of the invention syringe 12 is illustrated as being integrally formed with the housing 24. That is, for this and each of the other embodiments described herein, it is contemplated that the tube support housing 24 need not be a separate member, but can be molded of plastic, integrally with the syringe.

Figure 10:
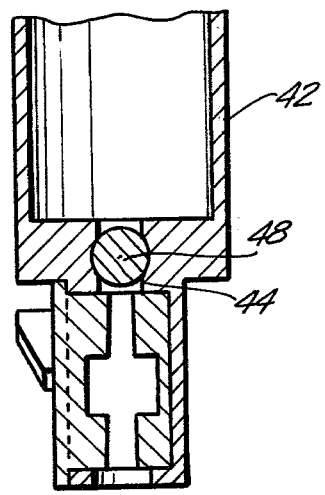
FIG. 10 is a sectional view taken along line 10—10 of FIG. 9.

In this embodiment of the invention base wall 45 of the housing is also made relatively thick, similar to that of the embodiment of FIG. 8, with a substantially straight port 44 formed therein. A thumb screw 46 is rotatably mounted in wall 45 perpendicularly to port 44 and passes through the port. The diameter of the shank 48 of the thumb screw is larger than the diameter of port 44, as seen in FIG. 10, so that the screw can close off port 44. In this embodiment, the physician can turn the screw down (i.e., inwardly into the housing) to close off port 44, create the suction in the syringe, insert the suction tube in the rotary support member 32, and thence insert the curette or suction tube through the cervix into the uterus of the patient. Once the inner end of the suction tube is properly positioned, the thumb screw can be removed or released, to open port 44 and apply the suction to the interior of the uterus in order to perform the curettage procedure. Should it be desired to change the tube size, or remove the instrument from the uterus without breaking the suction, the thumb screw 46 is simply turned down to again close off the port 44.

Of course, while one particular type of valve structure is shown in the embodiment of FIGS. 9 and 10, it is contemplated that other types of valve arrangements for selectively shutting off the port 44 can be provided. One such valve arrangement could be, for example, a simple slide valve structure.

Although illustrative embodiments of the present invention have been described herein with reference to the accompanying drawings, it is to be understood that the invention is not limited to those precise embodiments, and that various changes and modifications may be effected therein by one skilled in the art without departing from the scope or spirit of this invention.

What is claimed is:

1. A device for use in performing suction curettage procedures including a housing having at least one port therein through which the interior of the housing may communicate with a source of suction and a diametrically opposed opening therein, and a suction tube support member rotatably mounted in said housing; said tube support member having a plurality of intersecting and generally radially extending tube support bores of different diameters formed therein adapted to be selectively aligned between said housing port and opening, each of said bores being adapted to receive at least one differently sized suction tube therein through the housing opening whereby different tubes may be selectively connected to the housing and the source of suction.

2. A device as defined in claim 1 wherein said bores each having forward and rearward sections on opposite sides of the point of intersection with another bore and being respectively adapted to be aligned with the opening and port of the housing; at least said rearward sections of said bores being tapered in diameter from adjacent said point of intersection towards the end thereof to be positioned adjacent the housing port to frictionally receive therein two differently sized suction tubes.

3. A device as defined in claim 2 wherein the smallest diameter of each of the respective bores is at least as large as the internal diameter of the smallest tube to be frictionally received therein.

4. A device as defined in either of claims 1 or 2 wherein the diameter of said port is larger than the largest diameter of any of said bores.

5. A device as defined in claim 4 wherein said support member is removably mounted in said housing, said port is tapered and has its smallest diameter closer to said source of suction than to said support member and said housing opening is larger than the diameter of the largest tube to be used with the apparatus whereby upon removal of the support member from the housing permits insertion of tubes larger than can be received in the support member through said opening for support in said port.

6. A device as defined in claim 5 wherein the smallest diameter of the port is at least as large as the smallest diameter of the inside diameter of the largest tube to be inserted in the port.

7. A device as defined in claim 1 including valve means for selectively closing said port to prevent communication between the source of suction and a suction tube mounted in the housing.

8. A device as defined in claim 7 wherein said valve means comprises a separate valve member movably mounted in said housing for selectively blocking said port.

9. A device as defined in claim 7 wherein said valve means comprises a peripheral surface portion of said rotatable support member between two of said bores for blocking said port when positioned in juxtaposition therewith.

10. A device as defined in claim 9 wherein said housing opening is an elongated arcuate slot whereby said support member may be rotated between its port blocking position and a position wherein the port communicates with one of the bores while a suction tube is mounted on the support member.

11. A device as defined in claim 1 including a syringe body integrally formed with said housing; and a piston contained in the syringe; said syringe and piston defining said source of suction.

12. A device as defined in claim 1 wherein said housing includes a sleeve element adjacent said port and having an open end adapted to receive the forward end of a syringe, defining said source of suction, in relatively air tight engagement.

13. A device for use in performing suction curettage type procedures including a housing having a port formed therein adapted to communicate with a source of suction and a diametrically opposed opening through which a suction tube may be inserted into the housing, and a selectively positionable tube support member mounted in said housing between said port and said opening, said tube support member having a plurality of elongated bores of different diameters formed therein selectively positionable in alignment between said port and said housing; said bores each being tapered, at least in the end portion thereof adjacent said port to frictionally engage suction tubes of at least two different outside diameters therein; the smallest diameter of each bore being at least as large as the inside diameter of the smallest tube to be inserted therein and the diameter of the port being larger than the inside diameter of the largest suction tube to be supported in the support member whereby a plurality of different sized suction tubes may be selectively connected to said source of suction.

14. A device as defined in claim 13 wherein said tube support is a generally cylindrical member and is rotatably mounted in said housing and said bores extend along diameters of the housing in substantially the same plane, whereby said bores intersect each other.

15. A device as defined in either of claims 13 or 14 wherein said support member is removably mounted in said housing and said port is tapered and has its smallest diameter closer to said source of suction than to said support member; said housing opening being larger than the diameter of the largest tube to be used with the apparatus whereby upon removal of the support member from the housing permits insertion of tubes larger than can be received in the support member through said opening for support in said port.

16. A device as defined in claim 15 wherein the smallest diameter of the port is at least as large as the smallest diameter of the inside diameter of the largest tube to be inserted in the port.

17. A device as defined in claim 15 including valve means for selectively closing said port to prevent communication between the source of suction and a suction tube mounted in the housing.

18. A device as defined in claim 17 wherein said valve means comprises a separate valve member movably mounted in said housing for selectively blocking said port.

19. A device as defined in claim 17 wherein said valve means comprises a peripheral surface portion of said rotatable support member between two of said bores for blocking said port when positioned in juxtaposition therewith.

20. A device as defined in claim 19 wherein said housing opening is an elongated arcuate slot whereby said support member may be rotated between its port blocking position and a position wherein the port communicates with one of the bores while a suction tube is mounted on the support member.

21. A device as defined in claim 13 including a syringe body integrally formed with said housing; and a piston contained in the syringe; said syringe and piston defining said source of suction.

22. A device as defined in claim 13 wherein said housing includes a sleeve element adjacent said port and having an open end adapted to receive the forward end of a syringe, defining said source of suction, in relatively air tight engagement.

* * * * *